United States Patent
Mulac et al.

[11] Patent Number: 5,888,197
[45] Date of Patent: Mar. 30, 1999

[54] CAM-OPERATED UNIVERSAL LATCH JOINT APPARATUS

[75] Inventors: Anthony Mulac, East Jordan; Daniel Farley, Traverse, both of Mich.

[73] Assignee: Thompson Surgical Instruments, Inc., Traverse City, Mich.

[21] Appl. No.: 886,714

[22] Filed: Jul. 1, 1997

[51] Int. Cl.⁶ .................................................. A61B 17/00
[52] U.S. Cl. ......................................... 600/234; 403/396
[58] Field of Search .................................. 600/227, 228, 600/229, 230, 231, 234, 201; 403/396, 398, 385, 389, 391, DIG. 8

[56] References Cited

U.S. PATENT DOCUMENTS

| | | | |
|---|---|---|---|
| 4,949,707 | 8/1990 | LeVahn et al. | 600/234 |
| 5,020,195 | 6/1991 | LeVahn | 600/234 X |
| 5,242,240 | 9/1993 | Gorham | 403/391 |
| 5,727,899 | 3/1998 | Dobrovolny | 403/389 |
| 5,792,046 | 8/1998 | Dobrovolny | 600/234 |

*Primary Examiner*—Jeffrey A. Smith
*Attorney, Agent, or Firm*—McAndrews, Held & Malloy, Ltd.

[57] ABSTRACT

A cam-operated universal latch joint apparatus is provided. In an embodiment, the joint apparatus includes a cam locking mechanism, as well as a first clamping member and a second clamping member independently positionable with respect to each other. The second clamping member has an upper portion and a lower portion arranged adjacent to each other. A latch is pivotably mounted the upper portion of the second clamping member so that the latch selectively engages the lower portion of the second clamping member. Also, a through rod connecting the cam locking mechanism, the first clamping member and the second clamping member is provided. A bushing is also arranged between the upper portion of the second clamping member and the first clamping member. In an embodiment, the cam locking mechanism includes a handle and a cam connected to the handle and pivotably connected to the through rod so that the cam engages the first clamping member when selectively positioned by the user using the handle.

12 Claims, 4 Drawing Sheets

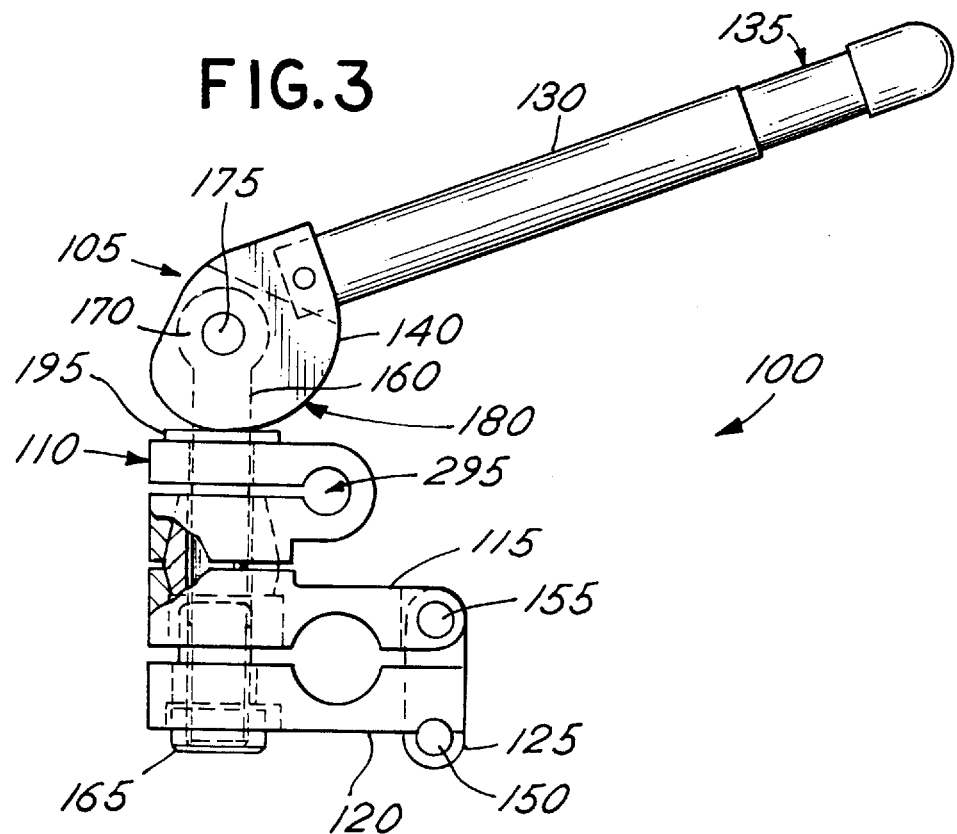
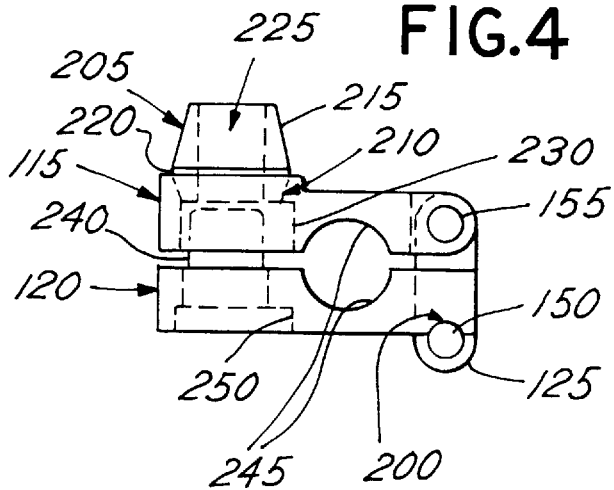

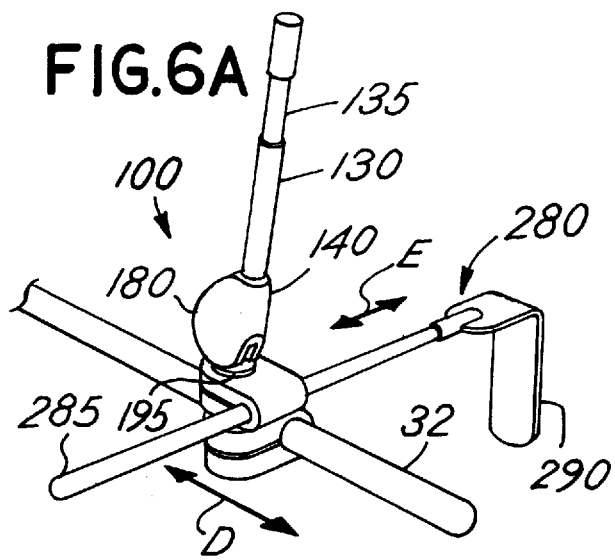
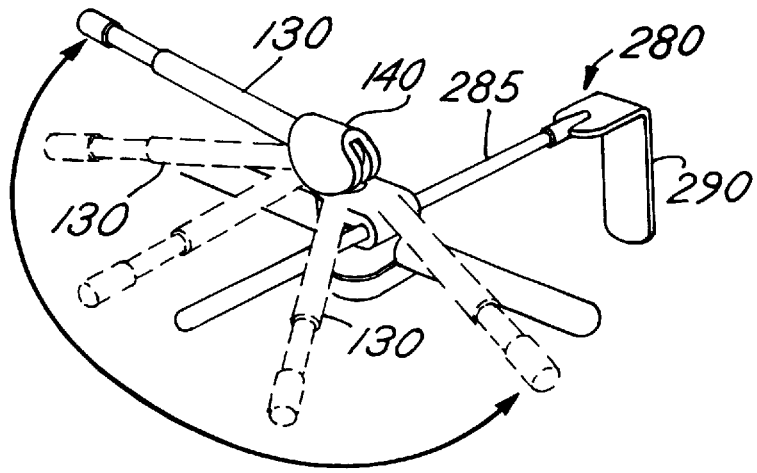
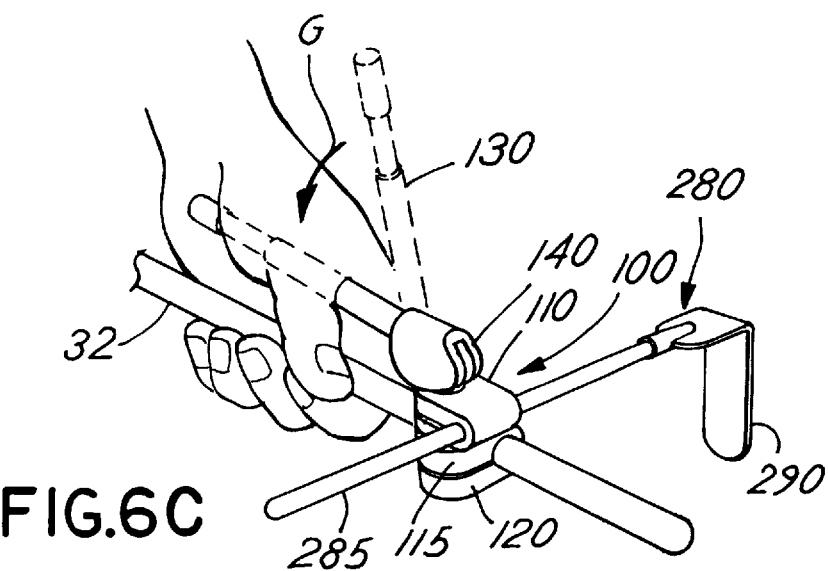

CAM-OPERATED UNIVERSAL LATCH JOINT APPARATUS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to a surgical apparatus for retracting a patient's anatomy to provide exposure of an operative site, and more particularly relates to a latch universal cam-operated joint apparatus which is sturdy, readily adjustable, easy to use, conducive to thorough sterilization, and suited for use in conjunction with a tubular frame stretcher or operating room table.

In surgical operations, some type of retraction apparatus is needed to access internal organs and bone structures. Variance in types of surgery and patient size necessitate a device which is both adjustable and sturdy. Furthermore, the nature of a patient's injuries or the patient's condition may make it desirable to perform a surgical procedure while the patient remains on a tubular frame stretcher as opposed to transferring the patient to a conventional operating table. In addition, equipment sterilization requirements necessitate a device which can be thoroughly cleaned by conventional means in a safe and easy manner.

Heretofore, table mounted surgical retraction devices have utilized rail clamps. The first type of rail clamp commonly used may not be secured to an operating table without breaking the sterile field. During surgery, repositioning of this rail clamp must be performed by a non-sterile circulating nurse, thereby increasing the duration of the surgery. An example of such a rail clamp is disclosed in U.S. Pat. No. 4,617,916. Other examples of various rail clamps are described in U.S. Pat. Nos. 4,254,763 and 4,971,038.

In addition, surgical retraction devices utilize universal connecting joint mechanisms. Such joint mechanisms consists of several parts which allow the surgeon to swivel and/or rotate the retractor blades into place. Examples of such devices are disclosed in U.S. Pat. Nos. 3,221,743, 4,617,916, and 5,025,780.

However, moving such retractor blades requires loosening the universal joint, moving the retractor blade and then re-tightening the joint. It would be highly desirable to have a universal joint mechanism which permits quick tightening of the joint and ease of movement of the retractor blade.

Further, during many surgical procedures, most operating rooms utilize table mounted mechanical retractors. This eliminates the need for operating room personnel to hold the retractors during the surgical procedure. The table mounted retractor allows the retractor blades to be mounted to a frame that is mounted to the operating room table. The frame is erected around the operating field and then remains basically static throughout the procedure.

The rigidity of the frame provides a strong, stable platform to mount retractors. However, it is not as versatile as a human counterpart. Also, because the desired exposure is not always directed to the center of the operating site, many times retractors are needed to be positioned to elevate or push down on the margins of the incision. The rigidity of the frame limits the exact placement of the retractor blades especially with ring type retractors as disclosed in Gautier U.S. Pat. No. 3,965,890 and Cabrera U.S. Pat. No. 4,421,108. Another system is disclosed in U.S. Pat. Nos. 3,221,743 and 5,025,780. Also, a retractor disclosed in LeVahn U.S. Pat. Nos. 4,617,916; 4,718,151; 4,947,707; and 5,020,195 as well as a retractor disclosed in U.S. Pat. No. 5,242,240 to Gorham expand the blade positioning capabilities.

These retractors utilize a universal joint to connect the retractor blade to the frame. The universal joint provides the surgeon with greater flexibility in blade placement. The universal joint disclosed in a table mounted retractor in 3,221,743 describes a joint made up of two clamping members, a conical bushing, and a means for providing compressive forces. A similar clamp design is shown in the LeVahn patents mentioned above.

The universal joint is quite strong and versatile, however, if the surgeon wishes to add a retractor blade between two secured components, it is impossible to do so. To make it easier to add retractors between secured components, LeVahn developed a split universal joint shown in U.S. Pat. Nos. 4,617,916, 4,718,151, and 4,917,707 mentioned above. The split universal joint allows retractors to be added to the frame between secured components.

However, because it does not encircle the frame arm, it is not as strong as the standard joints and will slip under pressure. Furthermore, because of the number of components of the split universal joint, it is difficult to sterilize and reassemble.

An inventor of the present application solved the component problems by designing a one-piece universal joint as disclosed in U.S. Pat. No. 5,025,780. To overcome the split joints slipping problem, LeVahn disclosed a hinge clamp in U.S. Pat. No. 5,020,195 which encircles the frame arm giving the joint additional strength. However, a problem with the hinge joint is that it is cumbersome to use, and does not use a bushing so that it can be rotated easily. Also, once it is on the frame arm, it can be difficult to slide and position. In addition to the problems discussed above, all of the above joints incorporate a thread clamping means which requires lubrication and maintenance.

BRIEF SUMMARY OF THE INVENTION

It is therefore an advantage of the present invention to provide a latch universal cam operated joint capable of clamping to a frame arm between secured components. The joint utilizes a bushing and has integral construction and implements a cam locking mechanism to eliminate thread maintenance.

It is another advantage of the present invention to provide a joint that has a locking, floating handle design to allow the surgeon to position the handle in any direction to avoid interfering with the operation.

Another advantage of the present invention is that it encircles the frame arm for added strength.

A further advantage of the present invention is to provide a retraction system having a universal connecting joint mechanism that is easy to use and permits quick release and repositioning of attachments such as retractors.

DETAILED DESCRIPTION OF THE SEVERAL VIEWS OF THE DRAWING

FIG. 3 is a side view, in partial cross-section, of an embodiment of the latch universal cam-operated joint of the present invention.

FIG. 4 is a cross-sectional side view of a latch assembly portion of the embodiment of the latch universal cam-operated joint of FIG. 3.

FIGS. 6A–6C are perspective views further illustrating the operation of an embodiment of the latch universal cam-operated joint of the present invention including a retractor and blade connected thereto.

DETAILED DESCRIPTION OF THE INVENTION

Figure 1:
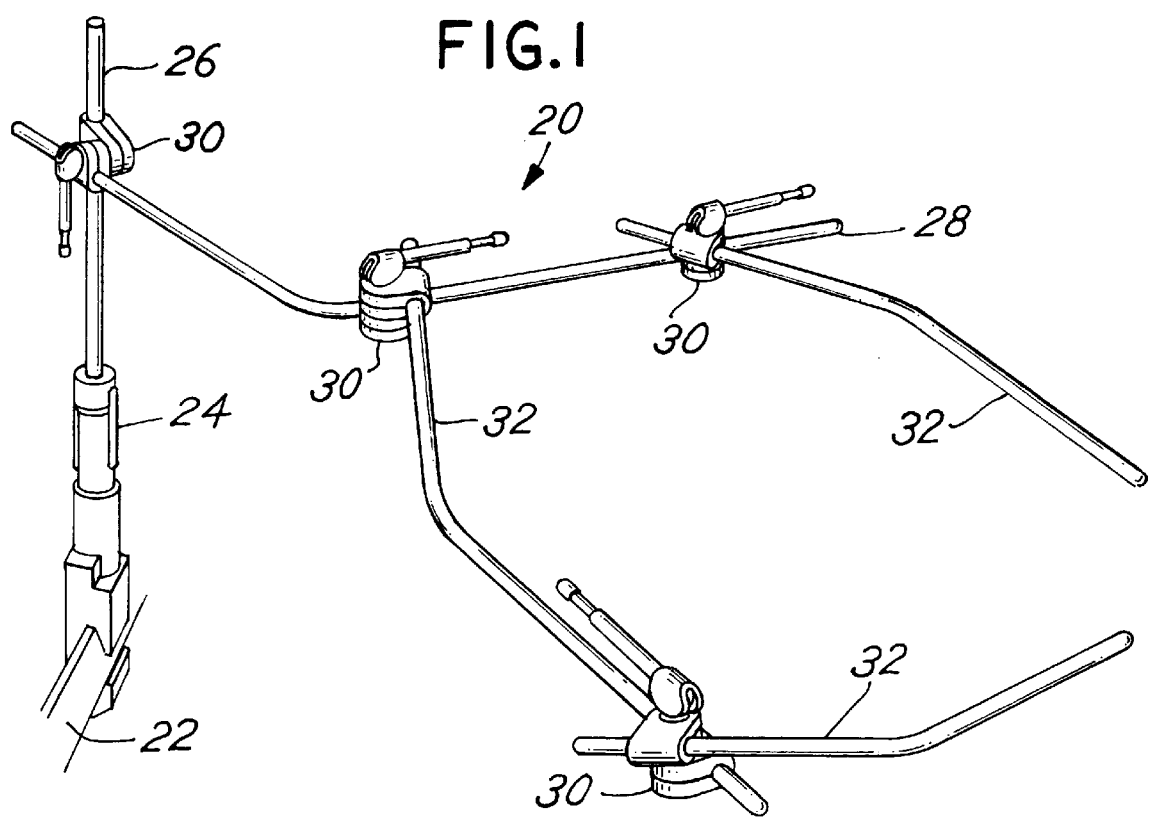
FIG. 1 is a perspective view of a support frame incorporating an embodiment of a latch universal cam-operated joint of the present invention.

FIG. 1 is perspective view of a frame referenced generally at 20 for use during surgical operations. The frame 20 consists of a mounting rail 22 having a rail clamp 24 connecting a vertical rod 26 to the rail 22. A crossbar 28 is connected to the vertical rod 26 by a cam operated joint 30. Similarly, a pair of angled arms 32 are connected to the crossbar 28 via similar universal joints 30. A further angled arm 32 is connected to one of the pair of angled arms 32 by another universal joint 30. With such a frame 20, as illustrated in FIG. 1, retractors discussed and illustrated below, may be connected to the angled arms 32 so that the retractors hold open an operative site of a patient without the necessity of human intervention. Thus, the retractors hold the operative site open for performing a procedure without requiring a member of the surgical team to hold the incision open by hand.

Figure 2:
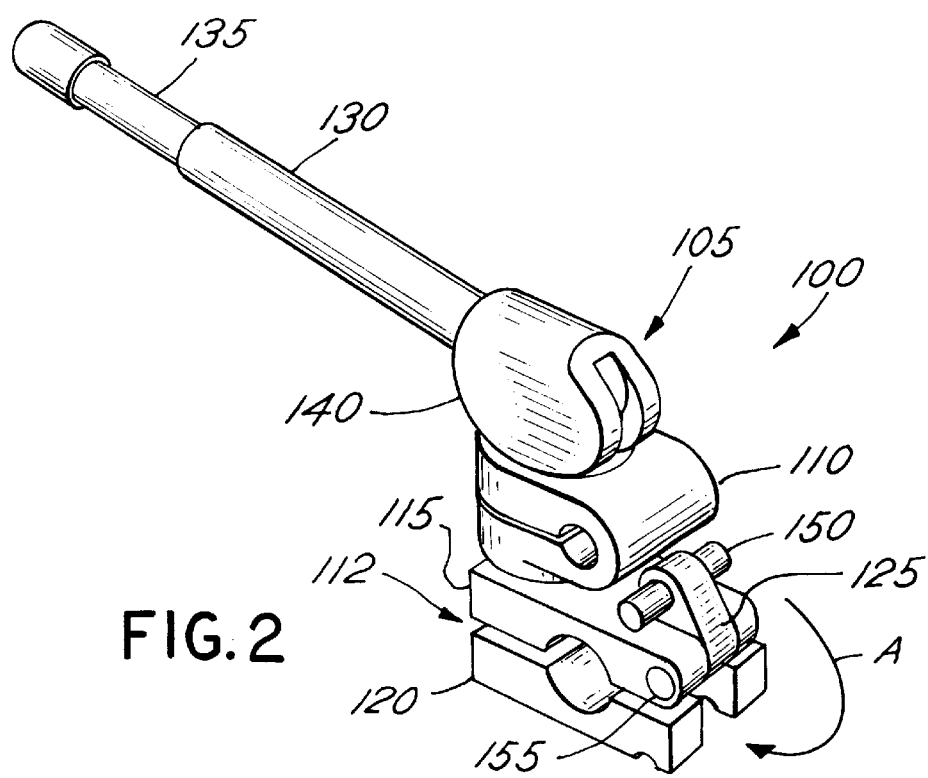
FIG. 2 is a perspective view of an embodiment of the latch universal cam-operated joint of the present invention.

FIG. 2 is a perspective view of an embodiment of the latch universal cam-operated joint of the present invention. The latch universal joint is referenced generally at 100. The latch universal joint 100 comprises unitary construction of a cam locking mechanism 105, a first clamping member 110, a second clamping member 112 having an upper portion 115 and a lower portion 120, and a latch 125.

The cam locking mechanism 105 further comprises a handle 130 having a recess 135 for easier gripping of the handle 130 by the user. The cam locking mechanism 105 also has a cam 140, the operation of which is described further below. The latch 125 further comprises a pin 150 and an axle 155. The latch 125 rotates on this axle 155. An arrow A indicates the direction of rotation of the latch 125 about the axle 155 acting as a pivot.

FIG. 3 is a side view including hidden lines illustrating the embodiment of the latch universal cam-operated joint 100 of FIG. 2, wherein like numerals represent like parts. FIG. 3 further includes a stud 160 arranged to align and connect the cam 140 to the first clamping member 110 and the upper and lower portion 115, 120 of the second clamping member 112 by means of a nut 165. The stud 160 also includes a eyelet portion 170 for accepting an axle 175 about which the cam 140 pivots. The cam 140 pivots on a cam surface 180. The cam surface 180 contacts a washer 195 which is preferably an anti-galling washer.

FIG. 4 is a side view of second clamping member 112 of the latch joint assembly of FIG. 3, wherein like numerals represent like parts. For example, the upper portion 115 and the lower portion 120 are shown connected by the latch 125 which pivots about the axle 155. A detent 200 is formed in the lower portion 120 of the second clamping member 112. The pin 150 of the latch 125 is seated in the detent 200 when in a locked position. Also, a bushing 205 is arranged in a bushing receiving bore 210 formed in the upper portion 115 of the second clamping member 112. The bushing 205 has a top tapered portion 215 and a bottom tapered portion 220. The bottom tapered portion 220 fits within the bushing receiving bore 210 as shown in FIG. 4. The bushing 205 also has through bore 225 through which the stud 160 passes.

In addition, an opening 230 is formed in the upper portion 115 of the second clamping member 112. The opening 230 is provided to receive a locating frame tab 240 that is formed in the lower portion of the second clamping member 112. The frame tab 240 acts to help align the upper portion 115 and the lower portion 120 to prevent twisting of the assembly. A notch 245 is formed in both the upper portion 115 and the lower portion 120 of the second clamping member 112. Further, a cutout portion 250 is provided in the lower portion 120 for receiving the head of the nut 165 shown in FIG. 3.

Figure 5A:
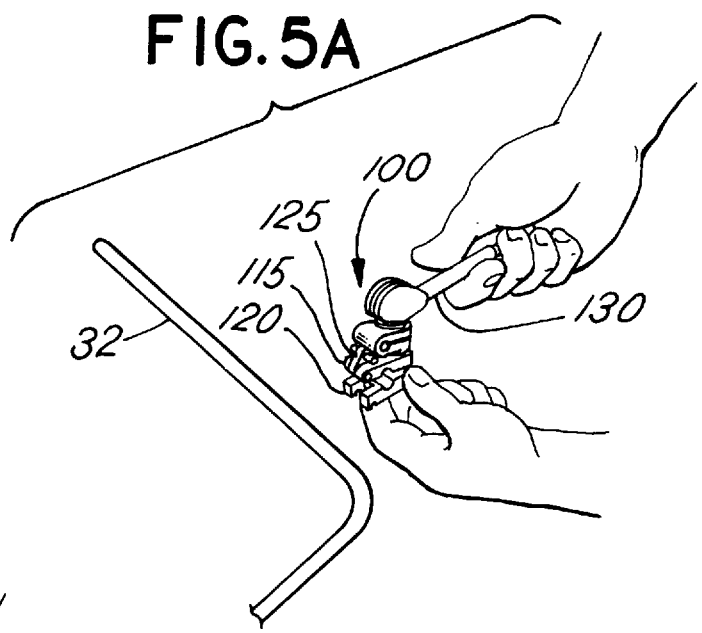
FIG. 5A–5C are perspective views illustrating successive steps of operating an embodiment of the latch universal cam operated joint to connect it to a support rod of the frame of FIG. 1.
Figure 5B:
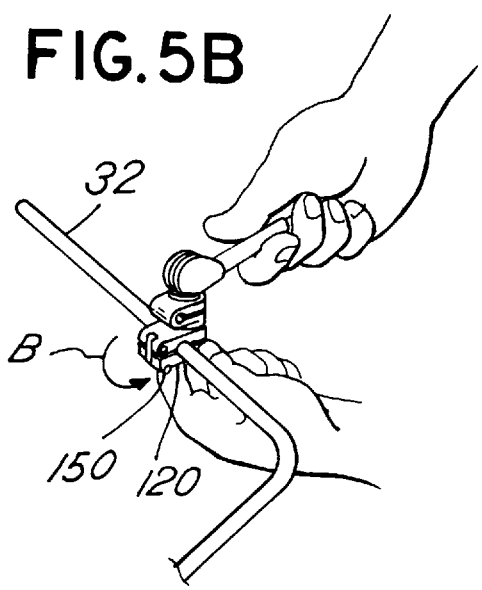
Figure 5C:
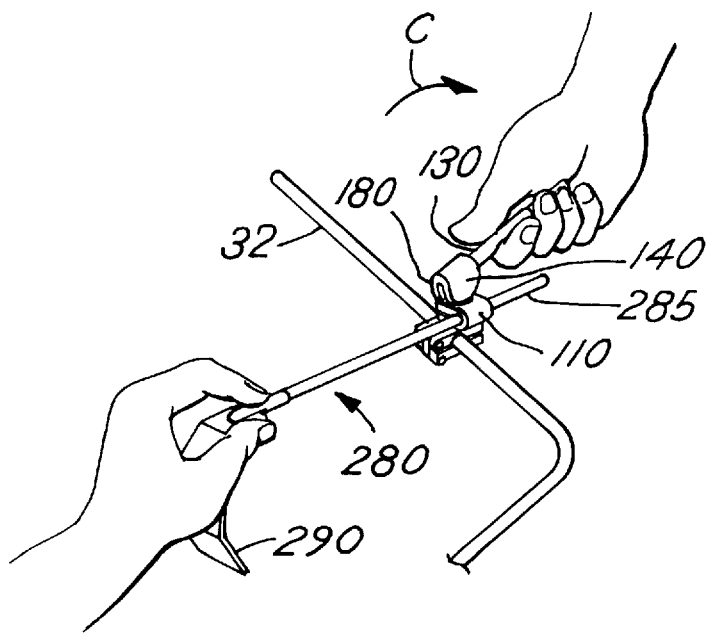

FIGS. 5A–5C illustrate how the embodiment of the latch universal cam-operated joint 100 of FIGS. 2–4 is operated in a typical procedure. For example, FIG. 5A illustrates angled arm 32 (see FIG. 1) and latch universal joint 100. The user manipulates the handle 130 so that the cam 140 is in an open position as shown. This enables the lower portion 120 to pivot downward from the upper portion 115 of the second clamping member 112. As illustrated, the latch 125 is an up position so that it does not obstruct the passage of the angled arm 32 from resting in the notch 245 formed in each of the upper and lower portions 115, 120 of the second clamping member 112. The user can then just slip the upper portion 115 and the lower portion 120 over the angled arm 32 in the position desired.

FIG. 5B illustrates how the latch 125 is engaged. The latch 125 is engaged by rotating as indicated by arrow B. The pin 150 comes to rest in the recess 200 of the lower portion 120. The joint 100 is now initially arranged for operation.

FIG. 5C illustrates how a retractor 280 is connected for performing an operation. The retractor 280 has a rod 285 and a blade 290. The blade 290 is placed into the incision in the patient to hold open the operative site. As shown in FIG. 5C, the rod 285 of the retractor 280 is positioned within the first clamping member 110 through an opening 295 (see FIG. 3). Once the retractor 280 is properly positioned in the operative site, the user rotates the handle 130 as indicated by arrow C to a desired location and locks the cam 140 via the pressure of the cam surfaces 180 against the anti-galling washer 195.

FIGS. 6A–6C further indicate the manipulation of the latch universal cam-operated joint 100. For example, FIG. 6A illustrates how the latch universal joint 100 is adjustably positionable along the angled arm 32 as indicated by arrow D. In addition, FIG. 6A illustrates how the retractor 280 is adjustable toward and away from the angled arm 32 as indicated by arrow E. The cam 140 is shown in an up, or open, position so that the cam surfaces 180 are not compressing the anti-galling washer 195. This allows the movement of the latch universal joint 100 along the angled arm 32.

FIG. 6B illustrates the beneficial feature of the floating cam arm which allows the user to position the handle 130 away from the operative site or other instruments in a position that is convenient. The handle 130 is shown in various positions in a rotation indicated by arrow F.

FIG. 6C illustrates the locking of the cam 140. The handle 130 is manipulated in a direction indicated by arrow G to tighten the cam surfaces 180 against the anti-galling washer 195. This locks the cam universal joint 100 in place.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A universal latch joint apparatus comprising:
   a cam locking mechanism;
   a first clamping member;
   a second clamping member having an upper portion and a lower portion arranged adjacent to each other;
   a latch pivotably mounted to the upper portion of the second clamping member such that the latch selectively engages the lower portion of the second clamping member; and
   a through rod connecting the cam locking mechanism, the first clamping member and the second clamping member.

2. The apparatus of claim 1 wherein the latch rotates between at least a first position and a second position so that the latch engages the lower portion when in the second position.

3. The apparatus of claim 1, further comprising:
   a bushing arranged between the upper portion and the first clamping member.

4. The apparatus of claim 1 wherein the latch has a locking pin arranged to engage the lower portion of the second clamping member.

5. The apparatus of claim 4 wherein the lower portion has a recess for accepting the pin on the latch.

6. The apparatus of claim 1 wherein the cam locking mechanism comprises:
   a handle; and
   a cam connected to the handle and pivotably connected to the through rod so that the cam engages the first clamping member when selectively positioned by using the handle.

7. The apparatus of claim 6 wherein the handle has a recessed portion.

8. The apparatus of claim 1 wherein the first clamping member has a receiving aperture formed therein.

9. The apparatus of claim 1 wherein the second clamping member has a notch portion.

10. The apparatus of claim 1 wherein the through rod further comprises an eyehole formed at an end thereof.

11. The apparatus of claim 10 further comprising an axle arranged in the cam locking mechanism, the axle passing through the eyehole of the through rod.

12. The apparatus of claim 1 wherein the cam locking mechanism, the first clamping member and the second clamping member are independently rotatable with respect to each other.

* * * * *